(12) United States Patent
Mozdzierz

(10) Patent No.: US 9,782,173 B2
(45) Date of Patent: Oct. 10, 2017

(54) CIRCULAR STAPLING DEVICE INCLUDING BUTTRESS RELEASE MECHANISM

(71) Applicant: Covidien LP, Mansfield, MA (US)

(72) Inventor: Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 692 days.

(21) Appl. No.: 14/186,289

(22) Filed: Feb. 21, 2014

(65) Prior Publication Data

US 2014/0252062 A1 Sep. 11, 2014

Related U.S. Application Data

(60) Provisional application No. 61/774,071, filed on Mar. 7, 2013.

(51) Int. Cl.
*A61B 17/072* (2006.01)
*A61B 17/115* (2006.01)

(52) U.S. Cl.
CPC .... *A61B 17/07292* (2013.01); *A61B 17/1155* (2013.01); *A61B 2017/07257* (2013.01); *A61B 2017/07271* (2013.01)

(58) Field of Classification Search
CPC ................ A61B 17/07292; A61B 2017/07257
USPC ...................................... 227/175.1
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |

(Continued)

FOREIGN PATENT DOCUMENTS

| | | |
|---|---|---|
| CA | 2282761 A1 | 9/1998 |
| CA | 2 667 434 A1 | 5/2008 |

(Continued)

OTHER PUBLICATIONS

Extended European Search Report corresponding to EP 13 19 2123.1, completed Jan. 30, 2014 and mailed Feb. 10, 2014; (8 pp).

(Continued)

*Primary Examiner* — Andrew M Tecco
*Assistant Examiner* — Chelsea Stinson

(57) ABSTRACT

A circular stapling device includes a handle assembly, an elongated body, an end effector, and one or more buttress members. The elongated body extends from the handle assembly. The end effector is mounted on a distal end of the elongate body and supports the one or more buttress members. A buttress release mechanism operatively coupled to the end effector selectively secures the one or more buttress members to the end effector.

14 Claims, 8 Drawing Sheets

(56) References Cited

U.S. PATENT DOCUMENTS

| | | |
|---|---|---|
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A * | 3/1995 | Carroll ............ A61B 17/07207 128/898 |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,009,034 B2 | 3/2006 | Pathak et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |

(56) References Cited

U.S. PATENT DOCUMENTS

| | | |
|---|---|---|
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,735,704 B2* | 6/2010 | Bilotti .............. A61B 17/072 227/175.1 |
| 7,744,627 B2 | 6/2010 | Orban, III et al. |
| 7,776,060 B2* | 8/2010 | Mooradian .......... A61B 17/115 227/180.1 |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,038,045 B2 | 10/2011 | Bettuchi et al. |
| 8,062,330 B2 | 11/2011 | Prommersberger et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,127,975 B2 | 3/2012 | Olson et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,178,746 B2 | 5/2012 | Hildeberg et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,071 B1* | 11/2012 | Knodel ............ A61B 17/07292 227/175.1 |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2* | 2/2013 | Aranyi ............ A61B 17/07207 227/175.1 |
| 8,371,493 B2* | 2/2013 | Aranyi ............ A61B 17/07207 227/175.1 |
| 8,393,514 B2 | 3/2013 | Shelton, Iv et al. |
| 8,408,440 B2 | 4/2013 | Olson et al. |
| 8,413,869 B2 | 4/2013 | Heinrich |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,584,920 B2 | 11/2013 | Hodgkinson |
| 8,590,762 B2 | 11/2013 | Hess et al. |
| 8,616,430 B2 | 12/2013 | Stopek et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,684,250 B2 | 4/2014 | Bettuchi et al. |
| 8,721,703 B2 | 5/2014 | Fowler |
| 8,757,466 B2 | 6/2014 | Olson et al. |
| 8,789,737 B2 | 7/2014 | Hodgkinson et al. |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |

(56) References Cited

U.S. PATENT DOCUMENTS

| | | |
|---|---|---|
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,773 B2 | 5/2016 | Casasanta, Jr. et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,364,229 B2 | 6/2016 | D'Agostino et al. |
| 9,364,234 B2 | 6/2016 | Stopek et al. |
| 9,433,412 B2 | 9/2016 | Bettuchi et al. |
| 9,433,413 B2 | 9/2016 | Stopek |
| 2002/0028243 A1 | 3/2002 | Masters |
| 2002/0086990 A1 | 7/2002 | Kumar et al. |
| 2002/0091397 A1 | 7/2002 | Chen |
| 2002/0151911 A1 | 10/2002 | Gabbay |
| 2002/0165559 A1 | 11/2002 | Grant et al. |
| 2002/0165563 A1* | 11/2002 | Grant ............... A61B 17/072 606/151 |
| 2003/0065345 A1 | 4/2003 | Weadock |
| 2003/0078209 A1 | 4/2003 | Schmidt |
| 2003/0083676 A1 | 5/2003 | Wallace |
| 2003/0120284 A1 | 6/2003 | Palacios et al. |
| 2003/0181927 A1 | 9/2003 | Wallace |
| 2003/0183671 A1 | 10/2003 | Mooradian et al. |
| 2003/0196668 A1 | 10/2003 | Harrison et al. |
| 2003/0208231 A1 | 11/2003 | Williamson et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0149073 A1 | 7/2005 | Arani et al. |
| 2005/0154093 A1 | 7/2005 | Kwon et al. |
| 2005/0228446 A1* | 10/2005 | Mooradian ......... A61B 17/115 606/215 |
| 2006/0004407 A1 | 1/2006 | Hiles et al. |
| 2006/0008505 A1 | 1/2006 | Brandon |
| 2006/0085030 A1 | 4/2006 | Bettuchi et al. |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2007/0243227 A1 | 10/2007 | Gertner |
| 2007/0246505 A1* | 10/2007 | Pace-Floridia .. A61B 17/07207 227/175.1 |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0216855 A1 | 9/2008 | Nasca |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1* | 6/2010 | Olson ................. A61B 17/072 227/176.1 |
| 2010/0147923 A1 | 6/2010 | D'Agostino et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089375 A1 | 4/2011 | Chan et al. |
| 2011/0215132 A1 | 9/2011 | Aranyi et al. |
| 2011/0282446 A1* | 11/2011 | Schulte ............ A61B 17/00491 623/11.11 |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0083723 A1 | 4/2012 | Vitaris et al. |
| 2012/0145767 A1 | 6/2012 | Shah et al. |

(56) References Cited

U.S. PATENT DOCUMENTS

| | | |
|---|---|---|
| 2012/0156289 A1 | 6/2012 | Blaskovich et al. |
| 2012/0187179 A1 | 7/2012 | Gleiman |
| 2012/0197272 A1 | 8/2012 | Oray et al. |
| 2012/0241499 A1 | 9/2012 | Baxter, III et al. |
| 2012/0273547 A1 | 11/2012 | Hodgkinson et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0146641 A1 | 6/2013 | Shelton, IV et al. |
| 2013/0153633 A1 | 6/2013 | Casasanta, Jr. et al. |
| 2013/0153634 A1* | 6/2013 | Carter ............... A61B 17/072 227/176.1 |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0181031 A1 | 7/2013 | Olson et al. |
| 2013/0193186 A1 | 8/2013 | Racenet et al. |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0209659 A1 | 8/2013 | Racenet et al. |
| 2013/0221062 A1 | 8/2013 | Hodgkinson |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0256380 A1 | 10/2013 | Schmid et al. |
| 2013/0277411 A1 | 10/2013 | Hodgkinson et al. |
| 2013/0306701 A1* | 11/2013 | Olson ............... A61B 17/1155 227/175.1 |
| 2013/0306707 A1 | 11/2013 | Viola et al. |
| 2013/0310873 A1 | 11/2013 | Stopek et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0061281 A1 | 3/2014 | Hodgkinson |
| 2014/0084042 A1 | 3/2014 | Stopek et al. |
| 2014/0097224 A1 | 4/2014 | Prior |
| 2014/0117066 A1 | 5/2014 | Aranyi et al. |
| 2014/0130330 A1 | 5/2014 | Olson et al. |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2014/0263556 A1* | 9/2014 | Mozdzierz ......... A61B 17/1155 227/176.1 |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0058451 A1 | 3/2016 | (Tarinelli) Racenet et al. |
| 2016/0100834 A1 | 4/2016 | Viola et al. |
| 2016/0106430 A1 | 4/2016 | Carter et al. |
| 2016/0113647 A1 | 4/2016 | Hodgkinson |
| 2016/0157857 A1 | 6/2016 | Hodgkinson et al. |
| 2016/0174988 A1 | 6/2016 | D'Agostino et al. |

FOREIGN PATENT DOCUMENTS

| | | |
|---|---|---|
| CN | 101310680 A | 11/2008 |
| CN | 101332110 A | 12/2008 |
| DE | 19924311 A1 | 11/2000 |
| EP | 0 327 022 A2 | 8/1989 |
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 256 318 A1 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 A1 | 8/2009 |
| EP | 2 090 244 A2 | 8/2009 |
| EP | 2 090 252 A2 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 236 099 A1 | 10/2010 |
| EP | 2 258 282 A2 | 12/2010 |
| EP | 2 292 276 A2 | 3/2011 |
| EP | 2 311 386 A2 | 4/2011 |
| EP | 2 436 348 A1 | 4/2012 |
| EP | 2 462 880 A2 | 6/2012 |
| EP | 2 497 431 A1 | 9/2012 |
| EP | 2 517 637 A1 | 10/2012 |
| EP | 2 586 380 A1 | 5/2013 |
| EP | 2 604 195 A1 | 6/2013 |
| EP | 2 604 197 A2 | 6/2013 |
| EP | 2 620 105 A1 | 7/2013 |
| EP | 2 620 106 A2 | 7/2013 |
| EP | 2 630 922 A1 | 8/2013 |
| EP | 2 644 125 A2 | 10/2013 |
| EP | 2 762 091 A2 | 8/2014 |
| JP | 2000-166933 A | 6/2000 |
| JP | 2002-202213 A | 7/2002 |
| JP | 2007-124166 A | 5/2007 |
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 98/38923 A1 | 9/1998 |
| WO | 99/45849 A1 | 9/1999 |
| WO | 03/088845 A2 | 10/2003 |
| WO | 03082126 A1 | 10/2003 |
| WO | 03/094743 A1 | 11/2003 |
| WO | 03/105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |

(56) References Cited

FOREIGN PATENT DOCUMENTS

| WO | 2008057281 A2 | 5/2008 |
| WO | 2008109125 A1 | 9/2008 |
| WO | 2010075298 A2 | 7/2010 |
| WO | 2011143183 A2 | 11/2011 |
| WO | 2012044848 A1 | 4/2012 |

OTHER PUBLICATIONS

Extended European Search Report corresponding to EP 13 19 2111.6, completed Feb. 13, 2014 and mailed Feb. 27, 2014; (10 pp).
Extended European Search Report corresponding to EP 13 19 5919.9, completed Feb. 10, 2014 and mailed Mar. 3, 2014; (7 pp).
Extended European Search Report corresponding to EP 08 72 6500.5, completed Feb. 20, 2014 and mailed Mar. 3, 2014; (7 pp).
Extended European Search Report corresponding to EP 13 19 5019.8, completed Mar. 14, 2014 and mailed Mar. 24, 2014; (7 pp).
Extended European Search Report corresponding to EP 13 19 6816.6, completed Mar. 28, 2014 and mailed Apr. 9, 2014; (9 pp).
Extended European Search Report corresponding to EP 13 19 7958.5, completed Apr. 4, 2014 and mailed Apr. 15, 2014; (8 pp).
Extended European Search Report corresponding to EP 13 19 4995.0, completed Jun. 5, 2014 and mailed Jun. 16, 2014; (5 pp).
Extended European Search Report corresponding to EP 14 15 7195.0, completed Jun. 5, 2014 and mailed Jun. 18, 2014; (9 pp).
Extended European Search Report corresponding to EP 14 15 6342.9, completed Jul. 22, 2014 and mailed Jul. 29, 2014; (8 pp).
Extended European Search Report corresponding to EP 14 15 7997.9, completed Sep. 9, 2014 and mailed Sep. 17, 2014; (8 pp).
Extended European Search Report corresponding to EP 14 16 9739.1, completed Aug. 19, 2014 and Aug. 29, 2014; (7 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Chinese Notification of Reexamination corresponding to counterpart Int'l Appln. No. CN 201010517292.8 dated Jun. 2, 2015.
Extended European Search Report corresponding to counterpart Int'l Appln. No. EP 14 15 2060.1 dated Aug. 14, 2015.
Japanese Office Action corresponding to counterpart Int'l Appln. No. JP 2014-216989 mailed Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 mailed Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 mailed Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16 15 0232.3 dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 mailed May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
Extended European Search Report corresponding to counterpart Int'l Appln. No. EP 16 15 3647.9 dated Jun. 3, 2016.
Examination Report issued in corresponding European Appln. No. 14157997.9 dated Jun. 29, 2016.
European Search Report corresponding to EP 05 02 2585.3, completed Jan. 25, 2006 and mailed Feb. 3, 2006; (4 pp).
European Search Report corresponding to EP 06 00 4598, completed Jun. 22, 2006; (2 pp).
European Search Report corresponding to EP 06 01 6962.0, completed Jan. 3, 2007 and mailed Jan. 11, 2007; (10 pp).
International Search Report corresponding to International Application No. PCT/US2005/036740, completed Feb. 20, 2007 and mailed Mar. 23, 2007; (8 pp).
International Search Report corresponding to International Application No. PCT/US2007/022713, completed Apr. 21, 2008 and mailed May 15, 2008; (1 p).
International Search Report corresponding to International Application No. PCT/US2008/002981, completed Jun. 9, 2008 and mailed Jun. 26, 2008; (2 pp).

(56) References Cited

OTHER PUBLICATIONS

European Search Report corresponding to EP 08 25 1779, completed Jul. 14, 2008 and mailed Jul. 23, 2008; (5 pp).
European Search Report corresponding to EP 08 25 1989.3, completed Mar. 11, 2010 and mailed Mar. 24, 2010; (6 pp).
European Search Report corresponding to EP 10 25 0639.1, completed Jun. 17, 2010 and mailed Jun. 28, 2010; (7 pp).
European Search Report corresponding to EP 10 25 0715.9, completed Jun. 30, 2010 and mailed Jul. 20, 2010; (3 pp).
European Search Report corresponding to EP 05 80 4382.9, completed Oct. 5, 2010 and mailed Oct. 12, 2010; (3 pp).
European Search Report corresponding to EP 10 25 1437.9, completed Nov. 22, 2010 and mailed Dec. 16, 2010; (3 pp).
European Search Report corresponding to EP 09 25 2897.5, completed Feb. 7, 2011 and mailed Feb. 15, 2011; (3 pp).
European Search Report corresponding to EP 10 25 0642.5, completed Mar. 25, 2011 and mailed Apr. 4, 2011; (4 pp).
European Search Report corresponding to EP 11 18 8309.6, completed Dec. 15, 2011 and mailed Jan. 12, 2012; (3 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and mailed May 3, 2012; (10 pp).
European Search Report corresponding to EP 12 16 5609.4, completed Jul. 5, 2012 and mailed Jul. 13, 2012; (8 pp).
European Search Report corresponding to EP 12 15 8861.0, completed Jul. 17, 2012 and mailed Jul. 24, 2012; (9 pp).
European Search Report corresponding to EP 12 16 5878.5, completed Jul. 24, 2012 and mailed Aug. 6, 2012; (8 pp).
Extended European Search Report corresponding to EP 12 19 1035.0, completed Jan. 11, 2013 and mailed Jan. 18, 2013; (7 pp).
Extended European Search Report corresponding to EP 12 18 6175.1, completed Jan. 15, 2013 and mailed Jan. 23, 2013; (7 pp).
Extended European Search Report corresponding to EP 12 19 1114.3, completed Jan. 23, 2013 and mailed Jan. 31, 2013; (10 pp).
Extended European Search Report corresponding to EP 12 19 2224.9, completed Mar. 14, 2013 and mailed Mar. 26, 2013; (8 pp).
Extended European Search Report corresponding to EP 12 19 6904.2, completed Mar. 28, 2013 and mailed Jul. 26, 2013; (8 pp).
Extended European Search Report corresponding to EP 12 19 6911.7, completed Apr. 18, 2013 and mailed Apr. 24, 2013; (8 pp).
Extended European Search Report corresponding to EP 07 00 5842.5, completed May 13, 2013 and mailed May 29, 2013; (7 pp).
Extended European Search Report corresponding to EP 12 19 8776.2, completed May 16, 2013 and mailed May 27, 2013; (8 pp).
Extended European Search Report corresponding to EP 12 19 8749.9, completed May 21, 2013 and mailed May 31, 2013; (8 pp).
Extended European Search Report corresponding to EP 13 15 6297.7, completed Jun. 4, 2013 and mailed Jun. 13, 20131; (7 pp).
Extended European Search Report corresponding to EP 13 17 3985.6, completed Aug. 19, 2013 and mailed Aug. 28, 2013; (6 pp).
Extended European Search Report corresponding to EP 13 17 3986.4, completed Aug. 20, 2013 and mailed Aug. 29, 2013; (6 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report issued in corresponding European Application EP 15174146 dated Jan. 20, 2016.
European Office Action corresponding to counterpart Int'l Appln. No. EP 14 17 2681.0 dated May 13, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 mailed Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln. No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 mailed Jul. 26, 2016.
Japanese Office Action corresponding to counterpart Int'l Appln. No. JP 2012-268668 mailed Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 mailed Aug. 25, 2016.
Australian Patent Examination Report No. 1 corresponding to counterpart Int'l Appln. No. AU 2012261752 dated Sep. 6, 2016.
Japanese Office Action corresponding to counterpart Int'l Appln. No. JP 2014-252703 mailed Sep. 26, 2016.
European Office Action corresponding to counterpart Int'l Appln. No. EP 12 19 8776.2 dated Sep. 12, 2016.
Japanese Office Action corresponding to counterpart Int'l Appln. No. JP 2013-000321 mailed Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Chinese First Office Action corresponding to counterpart Int'l Application No. CN 2017030801164420 dated Mar. 13, 2017.

* cited by examiner

CIRCULAR STAPLING DEVICE INCLUDING BUTTRESS RELEASE MECHANISM

CROSS-REFERENCE TO RELATED APPLICATIONS

This application claims the benefit of and priority to U.S. Provisional Patent Application No. 61/774,071, filed Mar. 7, 2013, the entire disclosure of which is incorporated by reference herein.

TECHNICAL FIELD

The present disclosure relates to surgical stapling devices. More particularly, the present disclosure relates to circular stapling devices that support a buttress.

BACKGROUND

Fasteners have traditionally been used to replace suturing when joining various body structures such as, for example, the bowel or bronchus. Surgical stapling devices employed to apply these fasteners are generally designed to simultaneously cut and seal tissue to reduce the time and risks involved with anastomosis procedures.

Circular surgical stapling devices are employed by surgeons to sequentially or simultaneously apply one or more surgical fasteners, e.g., staples or two-part fasteners, to body tissue for the purpose of joining segments of body tissue together and/or for the creation of anastomoses. Circular surgical stapling devices generally include an annular fastener cartridge assembly that supports a plurality of annular rows of fasteners, an annular anvil assembly operatively associated with the fastener cartridge assembly which provides a surface against which the fasteners are formed upon a firing of the circular stapling device, and an annular blade for cutting tissue.

For most procedures, the use of bare fasteners, with the fasteners in direct contact with the patient's tissue, is generally acceptable. The integrity of the tissue will normally serve to prevent the fasteners from tearing out of the tissue and compromising the sealing before healing has occurred. However, in some surgical operations buttress materials are employed by surgeons in combination with circular stapling devices to bridge, repair and/or reinforce tissue defects within a patient. In particular, buttress materials reduce the trauma suffered by the patient, reduce the instances of leakage, reduce the instances of bleeding, and create a relatively strong bond between adjacent body tissues.

Accordingly, there is a need for reliably and removably attaching buttress material onto a circular stapling device so that the buttress material does not interfere with the operation of the device, remains on the device until after the fasteners are fired, and is convenient and easy to install and use.

SUMMARY

According to one aspect, a circular stapling device includes a handle assembly, an elongate body, a cartridge assembly, and a cartridge buttress member.

The elongate body extends from the handle assembly. The cartridge assembly is mounted on a distal end of the elongate body and is movable relative to the distal end of the elongate body between a first position and a second position. The cartridge assembly is positioned adjacent to the distal end of the elongate body in the first position and spaced from the distal end of the elongate body in the second position. The cartridge assembly includes a tissue engaging surface that extends to an annular edge.

The cartridge buttress member has a body portion and an extension portion. The extension portion extends from the body portion of the cartridge buttress member. When the cartridge assembly is disposed in the first position, the body portion is supported on the tissue engaging surface of the cartridge assembly and the extension portion extends over the annular edge so that the extension portion is secured between the elongate body and the cartridge assembly to maintain the buttress member supported on the cartridge assembly.

A spring assembly is secured between the cartridge assembly and the distal end of the elongate member. The spring assembly is adapted to pull the cartridge assembly toward the distal end of the elongate member to maintain the cartridge assembly in close approximation with the distal end of the elongate member when the cartridge assembly is disposed in the first position. The spring assembly includes one or more springs that provide a spring force sufficient to trap the extension portion of the cartridge buttress member between the elongate member and the cartridge assembly when the cartridge assembly is disposed in the first position. The one or more springs permit movement of the cartridge assembly to release the extension portion of the cartridge buttress member from between the elongate member and the cartridge assembly when the cartridge assembly is moved toward the second position.

The cartridge assembly includes one or more pushers that drive the cartridge assembly toward the second position upon the firing of the circular stapling device and against the spring force of the one or more springs. The cartridge assembly moves to the second position and releases the extension portion of the cartridge buttress member from between the elongate member and the cartridge assembly. The body portion of the cartridge buttress member separates from the tissue engaging surface of the cartridge assembly upon the formation of fasteners supported in fastener retaining slots defined in the tissue engaging surface of the cartridge assembly.

In embodiments, the cartridge assembly includes a knife assembly. The knife assembly includes a knife. The one or more pushers are operatively coupled to a first driver. The knife assembly is operatively coupled to a second driver. The first and second drivers are separate and independently operable relative to each other.

The circular stapling device, in certain embodiments, includes an anvil assembly that is selectively movable relative to the cartridge assembly between an approximated position and an unapproximated position. An anvil buttress member is supported on a tissue engaging surface of the anvil assembly. The anvil buttress member has a body portion and an extension portion that extends from the body portion thereof. The anvil assembly includes a clamping assembly that secures the extension portion of the anvil buttress member to the anvil assembly so that the body portion of the anvil buttress member is supported over a tissue engaging surface of the anvil assembly. The clamping assembly includes a clamp that is spring loaded to maintain the extension portion of the anvil buttress member secured to the anvil assembly.

The clamp includes a lockout assembly that retains the clamp in a locked arrangement to maintain the extension portion of the anvil buttress member secured to the anvil assembly. The knife is movable to position the lockout assembly in an unlocked arrangement so that the spring force from the spring loaded clamp moves the clamp to release the extension portion of the anvil buttress member.

In accordance with another aspect, a circular stapling device includes a handle assembly, an elongate body that extends from the handle assembly, an end effector mounted on a distal end of the elongate body, and an anvil buttress member supported on the anvil assembly.

The end effector includes an anvil assembly and a cartridge assembly. The anvil assembly is selectively movable relative to the cartridge assembly between an approximated position and an unapproximated position.

The anvil buttress member has a body portion and an extension portion that extends from the body portion. The anvil assembly includes a spring loaded clamp that secures the extension portion of the anvil buttress member to the anvil assembly so that the body portion of the anvil buttress member is supported over a tissue engaging surface of the anvil assembly.

In embodiments, the circular stapling device includes a knife assembly including a knife. The spring loaded clamp includes a lockout assembly that retains the spring loaded clamp in a locked arrangement to maintain the extension portion of the anvil buttress member secured to the anvil assembly. The knife is movable to position the lockout assembly in an unlocked arrangement. The spring loaded clamp is configured to release the extension portion of the anvil buttress member when the lockout assembly is disposed in the unlocked arrangement.

The cartridge assembly is movable relative to the distal end of the elongate body between a first position and a second position. The cartridge assembly is positioned adjacent to the distal end of the elongate body in the first position and spaced from the distal end of the elongate body in the second position.

The cartridge assembly supports a cartridge buttress member that is secured between the elongate body and the cartridge assembly when the cartridge assembly is disposed in the first position. A movement of the cartridge assembly to the second position releases the cartridge buttress member from between the elongate body and the cartridge assembly.

According to yet another aspect, an anvil assembly includes an anvil head, an anvil cap, and a buttress member. The anvil head defines an opening. The anvil cap includes a cap body and a protuberance that extends from the cap body. The protuberance is securable within the opening defined within the anvil head to secure the anvil cap to the anvil head. The buttress member includes a body portion and an extension portion that extends from the body portion. The extension portion is securable between the anvil cap and the anvil head when the protuberance is positioned within the opening defined within the anvil head. The anvil head supports a washer adjacent to the protuberance. The washer is engageable with the protuberance to separate the anvil cap and the anvil head and release the extension portion from between the anvil cap and the anvil head. The washer is movable into engagement with the protuberance to separate the anvil cap and the anvil head so that the extension portion releases from between the anvil cap and the anvil head. The protuberance is one or both peened and melted within the opening to prevent the anvil cap from detaching from the anvil head.

In accordance with still another aspect, the present disclosure is directed to a method for releasing a cartridge buttress member from a cartridge assembly of a circular stapling device. The method includes the steps of providing a circular stapling device including an elongate member having a cartridge assembly mounted on a distal end of the elongate body, the cartridge assembly including a cartridge buttress member supported on a tissue engaging surface of the cartridge assembly and being trapped between the elongate member and the cartridge assembly; and moving the cartridge assembly relative to elongate member to release the cartridge buttress member from the circular stapling device.

According to one aspect, the method involves the steps of selectively maintaining an extension portion of the cartridge buttress member sandwiched between a proximal surface of the cartridge assembly and a distal surface of the elongate member under a spring force sufficient to trap the extension portion of the cartridge buttress member between the elongate member and the cartridge assembly; driving the cartridge assembly against the spring force to separate the cartridge assembly and the elongate member relative to each other; releasing the extension portion of the cartridge buttress member from being trapped between the elongate member and the cartridge assembly; and forming fasteners supported in fastener retaining slots defined in the tissue engaging surface of the cartridge assembly to separate the cartridge buttress member from the tissue engaging surface of the cartridge assembly.

Other aspects, features, and advantages will be apparent from the description, drawings, and claims.

DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Figure 1:
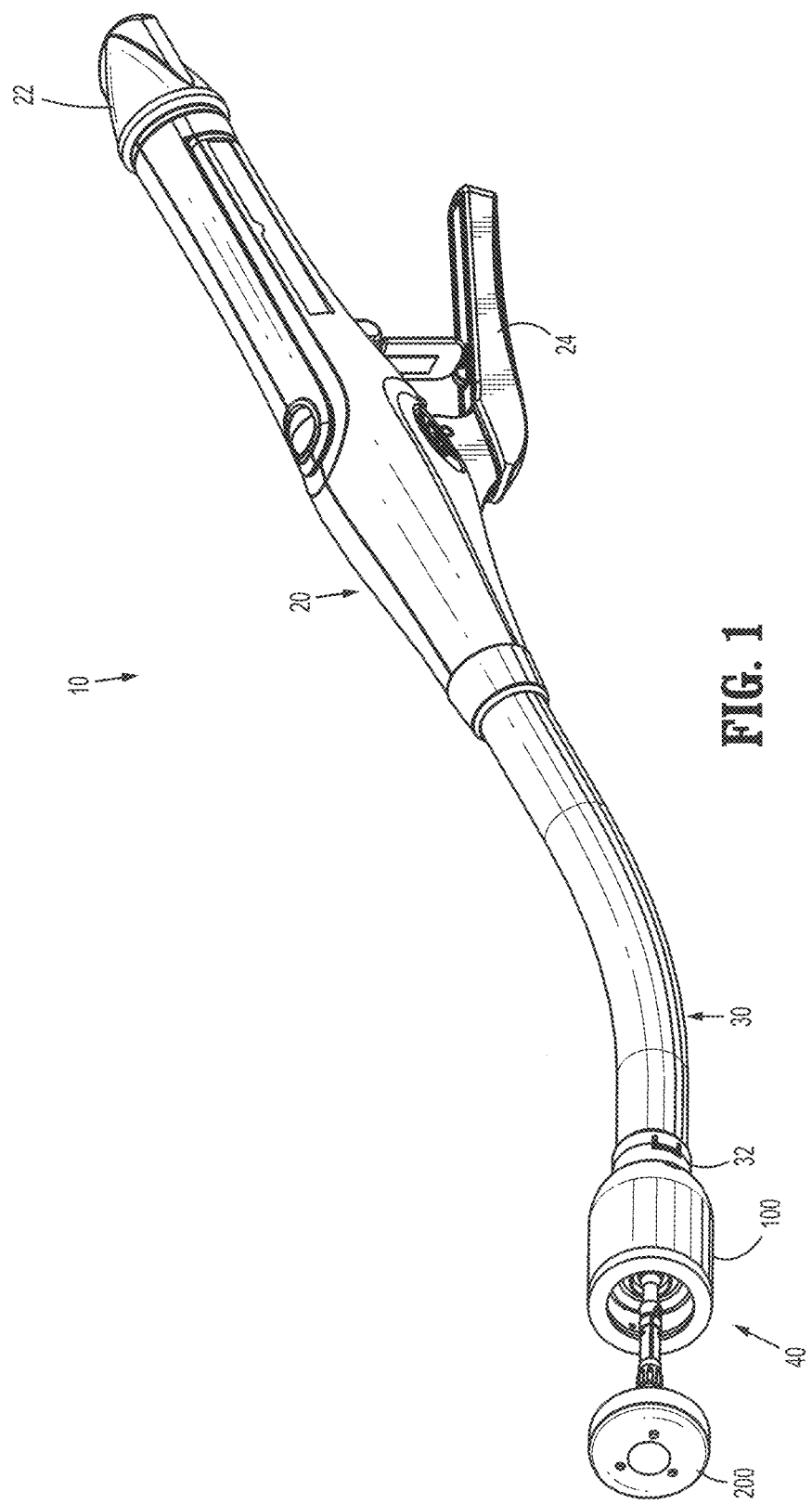
FIG. 1 is a perspective view of a circular stapling device according to the present disclosure.

As used herein, the term "clinician" refers to a doctor, a nurse, or any other care provider and may include support personnel. Particular embodiments of the present disclosure will be described herein with reference to the accompanying drawings. As shown in the drawings and as described throughout the following description, and as is traditional when referring to relative positioning on an object, the term "proximal" refers to the end of the device that is closer to the clinician and the term "distal" refers to the end of the device that is farther from the clinician. In the following description, well-known functions or constructions are not described in detail to avoid obscuring the present disclosure in unnecessary detail.

Referring initially to FIG. 1, a circular surgical stapling device for use with a buttress material is disclosed herein and is generally designated as 10. Surgical stapling device 10 includes a handle assembly 20, a tubular elongate body 30, and an end effector 40. The handle assembly 20 includes a rotatable advancing member 22 and a pivotable trigger member 24. The elongate body 30 extends distally from a distal end portion of the handle assembly 20 to a proximal end portion of the end effector 40 so that the elongate body 30 is disposed between the handle assembly 20 and the end effector 40. In some embodiments, the elongate body 30 has a linear shape along the length of the elongate body 30, and in certain embodiments, the elongate body 30 has a curved shape along the length of the elongate body 30.

A shell member 32 is supported on a distal end portion of the elongate body 30. The shell member 32 connects the proximal end portion of end effector 40 to the distal end portion of the elongate body 30. The end effector 40 can be integral with the body 30, or removable. The body 30 can be integral with the handle 20 or removable and replaceable. The body 30 and end effector 40 can be configured for use with an electro-mechanical, powered handle 500 (see FIG. 10) and/or console, or surgical robot.

The end effector 40 includes a fastener cartridge assembly 100, an anvil assembly 200, and a knife assembly with a substantially cylindrical knife 400 (FIG. 4) adapted to cut tissue. In embodiments, the fastener cartridge assembly 100 and/or the anvil assembly 200 may be replaced and the circular stapling device 10 may be reused.

In embodiments, the circular stapling device 10 is adapted for a single use and can be disposable. The circular stapling device 10 can include any number of drivers to effectuate a firing of the stapling device 10 including, for example, one driver that is operable to form fasteners supported by the end effector 40 and another driver that is operable to advance the knife 400 separate and/or independent of the other driver.

Reference may be made to U.S. Pat. No. 5,915,616 to Viola et al. and commonly owned U.S. Patent Application Publication No. 2011/0174099, filed on Nov. 15, 2010, entitled "Adapters for Use Between Surgical Handle Assembly and Surgical End Effector," the entire contents of which are hereby incorporated herein by reference, for a detailed discussion of the construction and operation of exemplary circular stapling devices.

Figure 2:
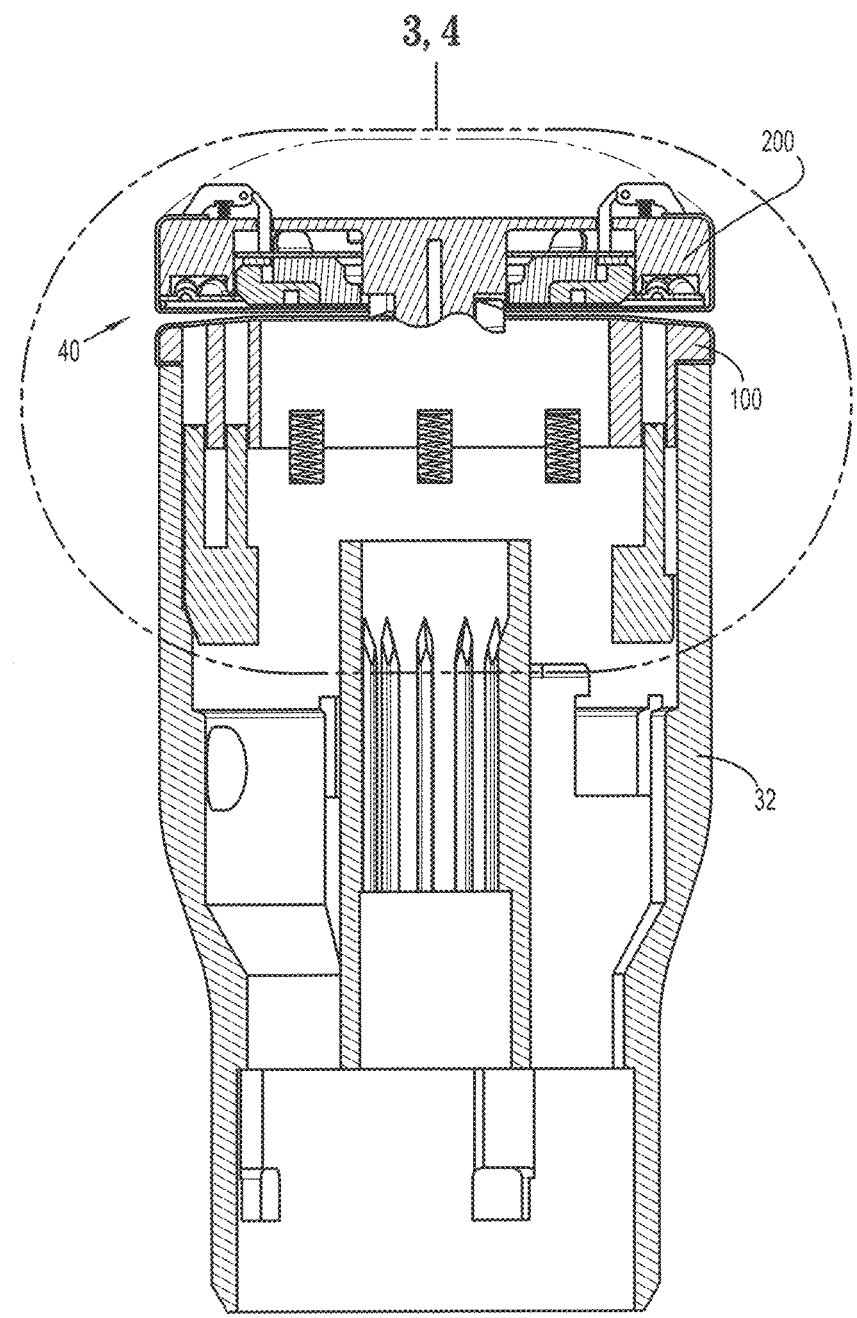
FIG. 2 is a cross-sectional view of an embodiment of an end effector of the circular stapling device of FIG. 1.
Figure 3:
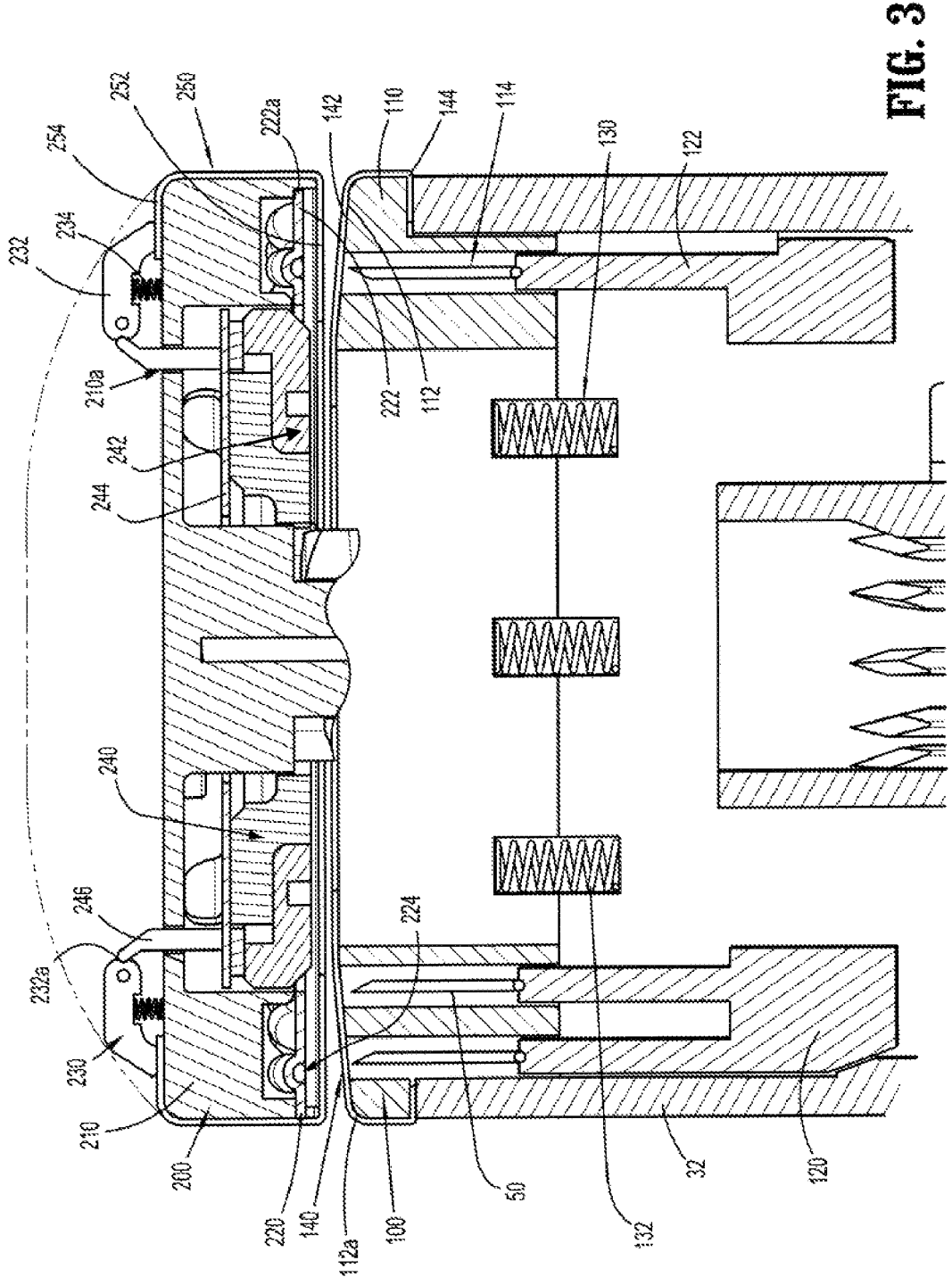
FIGS. 3 and 4 are progressive, enlarged, cross-sectional views of the indicated area of detail shown in FIG. 2.
Figure 4:
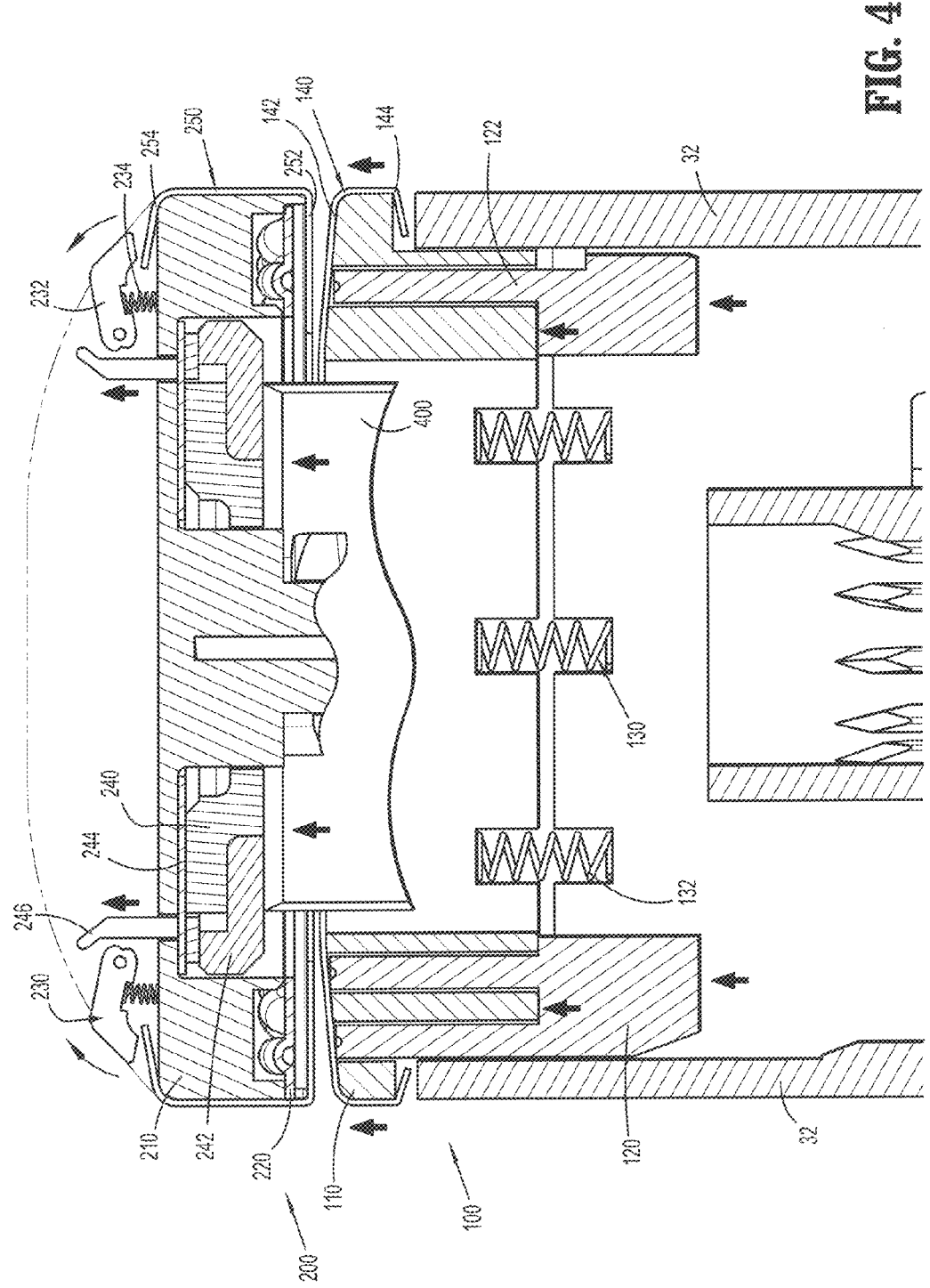

Turning now to FIGS. 2-4, the fastener cartridge assembly 100 is mounted on a distal end portion of the elongate body 30 and is movable relative to the distal end portion of the elongate body 30 between a first position and one or more second positions including any intermediate positions. In the first position, the cartridge assembly 100 is positioned adjacent to the distal end portion of the elongate body 30. In the second position, the cartridge assembly 100 is spaced from the distal end portion of the elongate body 30.

The fastener cartridge assembly 100 includes a cartridge body 110 and pusher member 120. The cartridge body 110 has a tissue engaging surface 112 that extends to an outer annular edge 112a and defines a plurality of fastener retaining slots 114 in an annular and/or concentric array about the tissue engaging surface 112. Each fastener retaining slot 114 is dimensioned to support a fastener 50 such as a surgical staple.

The pusher member 120, which is operatively coupled to a driver adapted to drive the pusher member 120, includes a substantially cylindrical body having a plurality of pushers 122 dimensioned to engage the fasteners 50 retained in the fastener retaining slots 114. The plurality of pushers 122 is disposed in an annular and/or concentric array about the cylindrical body of the pusher member 120. The plurality of pushers 122 drives the cartridge assembly 100 toward the second position upon the firing of the circular stapling device 10. The pusher member 120 is dimensioned to receive the knife 400 therethrough.

A spring assembly 130 is secured between the cartridge assembly 100 and the distal end portion of the elongate member 30. The spring assembly 130 is adapted to pull the cartridge assembly 100 toward the distal end portion of the elongate member 30 to maintain the cartridge assembly 100 in close approximation with the distal end portion of the elongate member 30, for example, when the cartridge assembly 100 is disposed in the first position. The spring assembly 130 includes one or more springs 132 secured between a proximal end portion of the cartridge body 110 and a distal end portion of the shell member 32 by any suitable fastening technique. The one or more springs 132, which may have any suitable spring constant, are adapted to pull or draw the cartridge body 110 toward the shell member 32 to maintain the proximal end portion of the cartridge body 110 in close approximation with the distal end portion of the shell member 32 as shown in FIG. 4. The one or more springs 132 are adapted to stretch from a compressed condition to an expanded condition to enable the proximal end portion of the cartridge body 110 to be unapproximated from the distal end portion of the shell member 32. The one or more springs could be helical in shape, but other configurations are contemplated. Alternatively, other resilient means may be used in addition to, or in place of the spring assembly 130.

Figure 9:
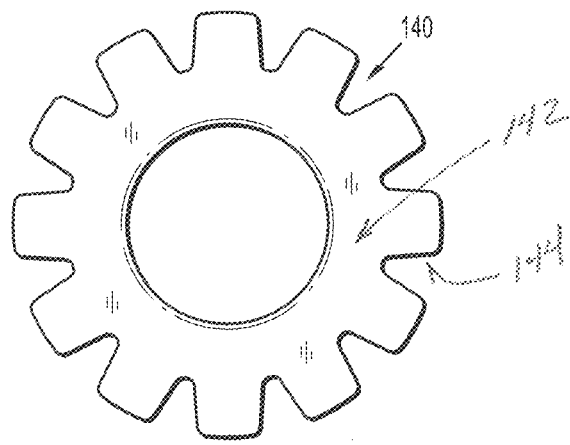

With reference to FIGS. 3, 4, and 9, a cartridge buttress member 140, has a body portion 142 and an extension portion 144 that extends from the body portion 142 of the cartridge buttress member 140. The extension portion 144 is dimensioned to extend over the annular edge 112a of the tissue engaging surface 112 of the cartridge body 110. The extension portion 144 is securable between the distal end portion of the shell member 32 and the proximal end portion of the cartridge body 110 to maintain the cartridge buttress member 140 supported on the cartridge body 110. For example, when the cartridge assembly 100 is disposed in the first position, the body portion 142 is supported on the tissue engaging surface 112 of the cartridge assembly 100 and the extension portion 144 extends over the annular edge 112a of the tissue engaging surface 112 so that the extension portion 144 is secured between the elongate body 30 and the cartridge assembly 100 to maintain the cartridge buttress member 140 supported on the cartridge assembly 100.

The one or more springs 132 of the spring assembly 130 provide a spring force sufficient to trap the extension portion 144 of the cartridge buttress member 140 between the elongate member 30 and the cartridge assembly 100. As described in greater detail below, the one or more springs 132 are movable with the cartridge assembly 100, and against the spring force of the one or more springs 132, to release the extension portion 144 of the cartridge buttress member 140 from between the elongate member 30 and the cartridge assembly 100 when the cartridge assembly 100 is moved toward the second position. In the second position, the body portion 142 of the cartridge buttress member 140 separates from the tissue engaging surface 112 of the cartridge assembly 100 upon or following the formation of the fasteners 50 supported in the fastener retaining slots 114.

Following the firing of the circular stapling device 10, the anvil assembly 200 is selectively movable relative to the cartridge assembly 100 between an approximated position and an unapproximated position. The anvil assembly 200 includes an anvil body 210, an anvil plate 220, a clamping assembly 230, and a crush assembly 240. The anvil body 210 defines one or more openings 210a and is supported between the clamp assembly 230 and the anvil plate 220. The anvil plate 220 has a tissue engaging surface 222 that extends to an annular edge 222a and defines a plurality of fastener forming pockets 224 that are disposed in an annular and/or concentric array about the tissue engaging surface 222. The clamping assembly 230 includes one or more clamps 232 and one or more springs 234 that spring load the one or more clamps 232. The one or more clamps 232 define a recess 232a. The crush assembly 240 includes one or more knife engaging members 242, a crush ring 244, and one or more clamp engaging fingers 246.

Figure 8:
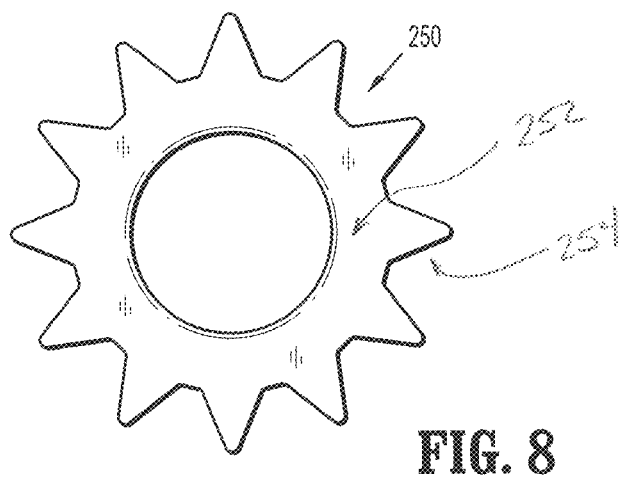

Referring also to FIG. 8, an anvil buttress member 250 has a body portion 252 and an extension portion 254 that extends from the body portion 252 of the anvil buttress member 250. The extension portion 254 is dimensioned to extend over the annular edge 222a of the tissue engaging surface 222 of the anvil plate 220. The extension portion 254 is securable between a proximal end portion of the clamping assembly 230 and a distal end portion of the anvil body 210 to maintain the extension portion 254 of the anvil buttress member 250 secured to the anvil assembly 200 so that anvil buttress member 250 is supported over the tissue engaging surface 222 of the anvil plate 220. For example, the clamping assembly 230 includes a lockout assembly comprising a distal end portion of the one or more clamp engaging fingers 246 and the recess 232a of the one or more clamps 232. As described in greater detail below, the distal end portion of the one or more clamp engaging fingers 246 cooperate to retain the one or more clamps 232 in a selectively locked arrangement to lock extension portion 254 of the anvil buttress member 250 against the distal end portion of the anvil body 210.

In operation, before a firing of the circular stapling device 10 and after a placement of the anvil assembly 200 and the fastener cartridge assembly 100 into a target surgical site, as described in U.S. Pat. No. 5,915,616 or U.S. Patent Application Publication No. 2011/0174099, the disclosures of which are hereby incorporated by reference in their entirety, the anvil assembly 200 and the fastener cartridge assembly 100 are positioned in an approximated condition by a drive assembly (not shown) to clamp tissue therebetween. As shown in FIGS. 2 and 3, with the cartridge assembly 100 and the anvil assembly 200 in the approximated condition, the spring assembly 130 urges the cartridge body 110 of the cartridge assembly 100 toward the distal end portion of the shell member 32 to trap a distal end portion of the extension portion 144 of the cartridge buttress member 140 between the distal end portion of the shell member 32 and the proximal end portion of the cartridge body 110, as described above. Similarly, under the contacting engagement of a distal end portion of the one or more clamp engaging fingers 246 of the crush assembly 240 with the recess 232a of the one or more clamps 232, the one or more clamps 232 of the clamping assembly 230 lock extension portion 254 of the anvil buttress member 250 against the distal end portion of the anvil body 210 to maintain the body portion 252 of the anvil buttress member 250 supported over the tissue engaging surface 222 of the anvil plate 220.

With reference again to FIG. 4, upon a firing of the circular stapling device 10, the pushers 122 of the pusher member 120 distally advance through the fastener retaining slots 114 to dispense the fasteners 50 from the fastener retaining slots 114. Upon being dispensed from the fastener retaining slots 114, the legs of the fasteners 50 are driven through the cartridge buttress member 140, the clamped tissue, and the anvil buttress member 250, before being formed against the fastener forming pockets 224 defined in the tissue engaging surface 222 of the anvil plate 220. As the pusher member 120 distally advances, the pusher member 120 engages the cartridge body 110 and drives the cartridge body 110 distally away from the shell member 32 against the opposing forces of the one or more springs 132. The separation of the cartridge body 110 from the shell member 32 provides a space between the cartridge body 110 and the shell member 32 sufficient to enable the extension portion 144 of the cartridge buttress member 140 to release from between the cartridge body 110 and the shell member 32.

The knife 400 is distally advanceable by a driver of a drive assembly (not shown) through the cartridge assembly into engagement with the knife engaging members 242 of the crush assembly 240. As the knife 400 drives the knife engaging members 242 distally, the knife engaging members 242 compress the crush ring 244 and drive the clamp engaging fingers 246 distally through the openings 210 a defined in the anvil body 210. The distal movement of the clamp engaging fingers 246 disengages the distal end portion of the clamp engaging fingers 246 from the recess 232a of the one or more clamps 232 of the clamp assembly 230 and thus, repositions the lockout assembly in an unlocked arrangement to allow the one or more clamps 232 to completely disengage from the clamp engaging fingers 246. Under the spring force of the one or more springs 243, the one or more springs 234 urge the one or more clamps 232 away from the distal end portion of the anvil body 210 and free the distal end portions of the extension portion 254 of the anvil buttress member 250, enabling the entire anvil buttress member 250 to separate from the anvil assembly 200.

Figure 5:
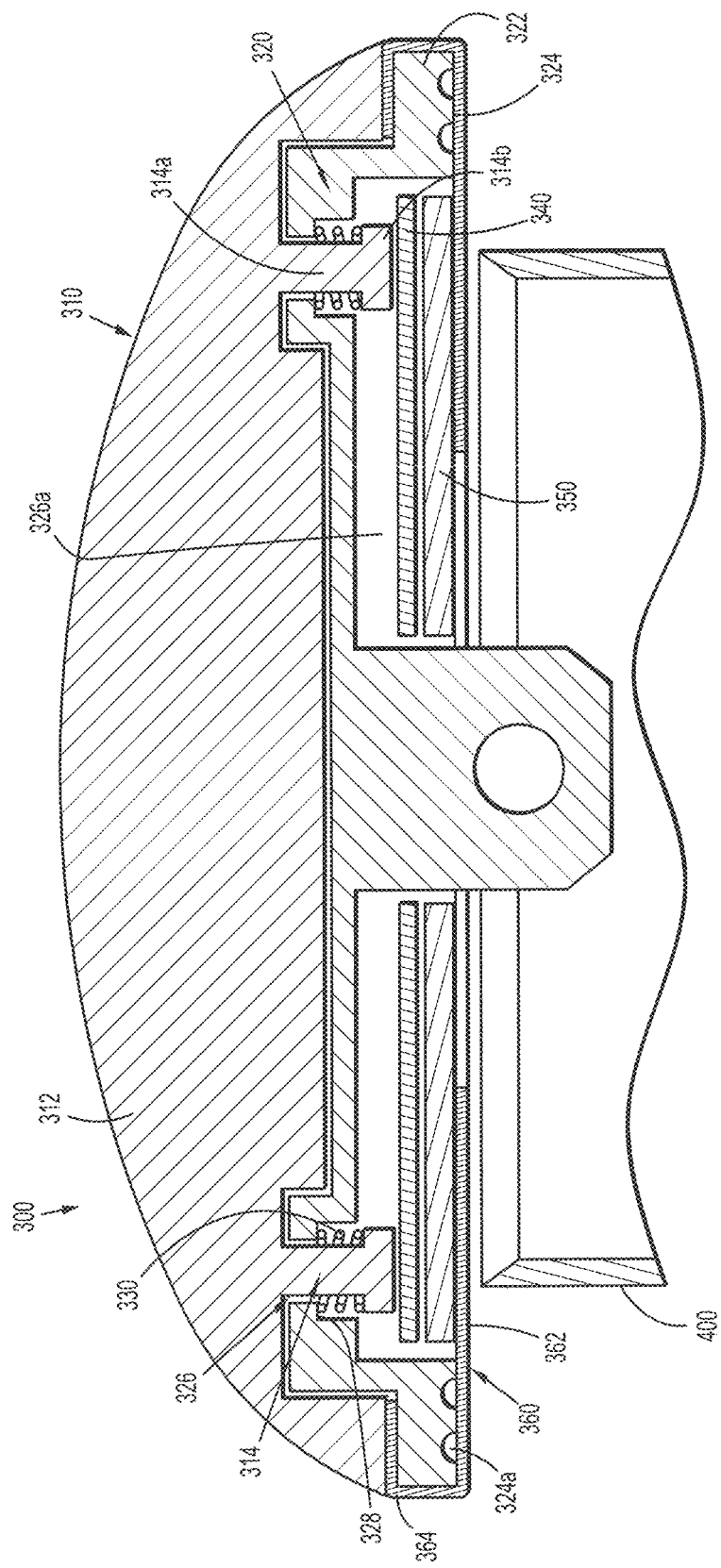
FIGS. 5 and 6 are progressive, enlarged, cross-sectional views of a portion of another embodiment of an end effector of the circular stapling device of FIG. 1.
Figure 6:
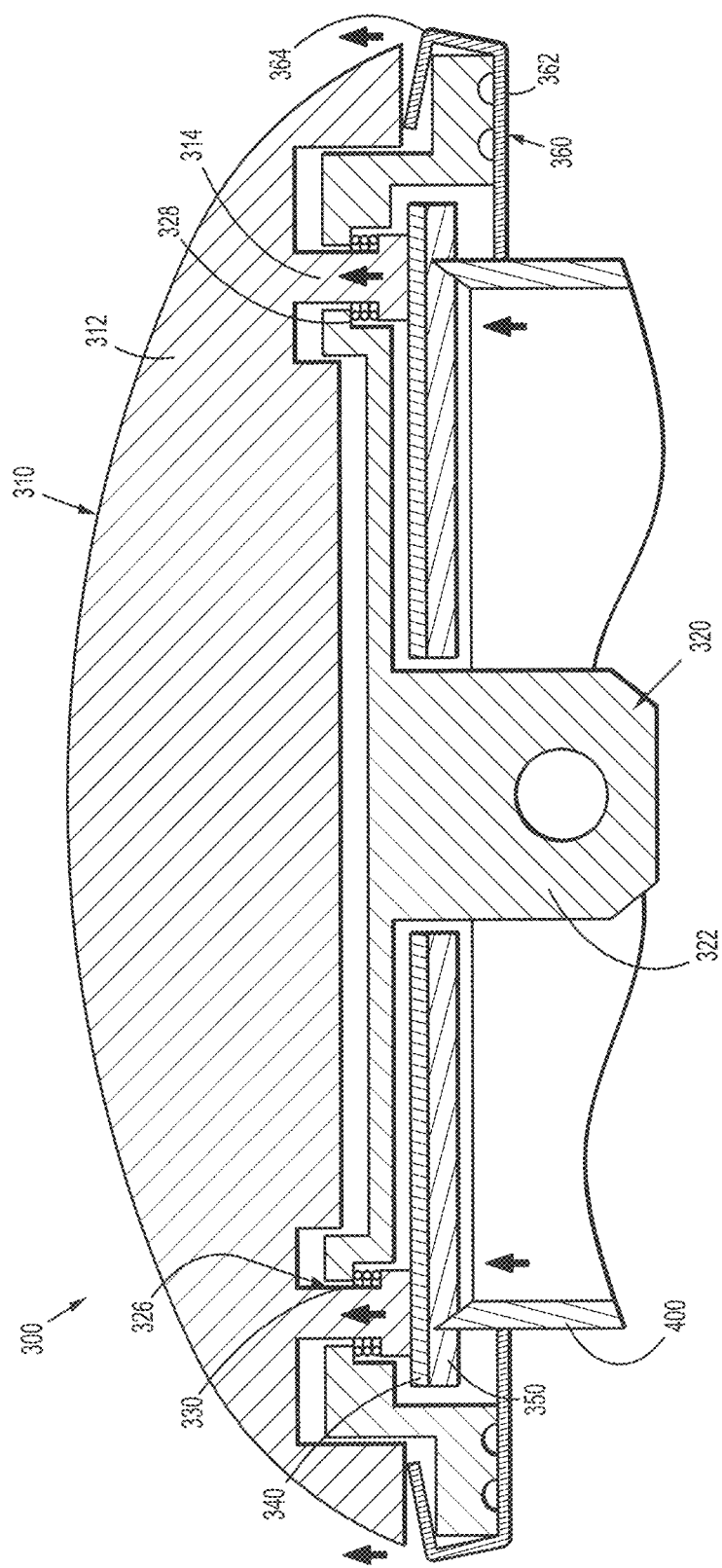
Figure 7:
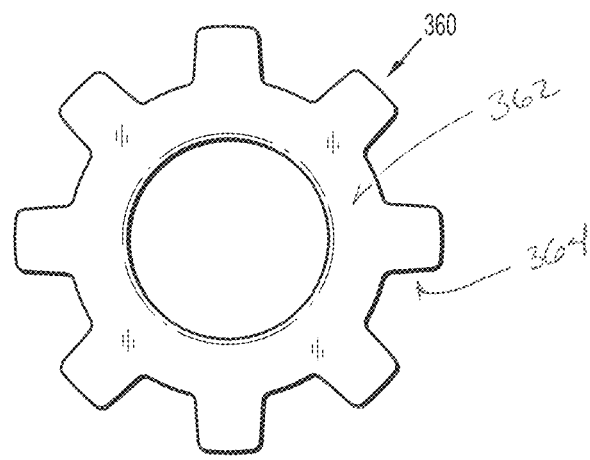
FIGS. 7-9 are top plan views of exemplary anvil and/or cartridge surgical buttress members.

Turning now to FIGS. 5 and 6, another embodiment of an anvil assembly is generally referred to as anvil assembly 300. Anvil assembly 300 includes an anvil cap 310, an anvil head 320, a biasing member 330 (e.g., a spring), a washer 340, a cut ring 350, and an anvil buttress member 360 (FIG. 7).

The anvil cap 310 is selectively movable between approximated and unapproximated positions relative to the anvil head 320 and includes a cap body 312 having one or more protuberances 314 extending proximally from the cap body 312. Each protuberance 314 includes an arm member 314a and a cross member or head portion 314b. The arm member 314a extends proximally from a proximal end portion of the cap body 312 and supports the cross member 314b on a proximal end portion of the arm member 314a.

The anvil head 320 includes a head body 322 with a tissue engaging surface 324. The tissue engaging surface 324 defines a plurality of fastener forming pockets 324a. The head body 322 defines one or more openings 326 in a distal end portion of the head body 322 and a central opening 326a in a proximal end portion of the head body 322. The central opening 326a is dimensioned to receive the washer 340 and the cut ring 350 and each opening 326 is dimensioned to receive a protuberance 314 of the anvil cap 310 therein to secure the anvil cap 310 to the anvil head 320. Each protuberance 314 can be one or both peened and melted within the one or more openings 326 to prevent the anvil cap 310 from detaching from the anvil head 320. When received in the central opening 326a, the washer 340 can be positioned adjacent to the protuberance 314 of the anvil cap 310. The biasing member 330 is positioned about the arm member 314a of the protuberance 314 between shoulders 328 of the cap body 322 and the cross member 314b of the protuberance 314 to urge a proximal end portion of the anvil cap 310 into approximation with a distal end portion of the anvil head 320. As seen in FIG. 7, the anvil buttress member 360 includes a body portion 362 and an extension portion 364 that extends from the body portion 362. The extension portion 364 is securable between the anvil cap 310 and the anvil head 320 when the protuberance 314 is positioned within the one or more openings 326 defined within the anvil head 320.

In operation, the knife 400 is advanced distally under a distal driving force into engagement with the cut ring 350. The distal driving force drives the washer 340 into engagement with a distal end portion of the cross member 314*b* of the one or more protuberances 314 of the anvil cap 310 and compresses the biasing member 330 between the distal end portion of the cross member 314*b* of the anvil cap 310 and the proximal end portion of the shoulders 328 of the anvil head 320. The engagement of the washer 340 with the one or more protuberances 314 separates the anvil cap 310 from the anvil head 320. As the anvil cap 310 separates from the anvil head 320, a proximal end portion of the anvil cap 310 separates from a distal end portion of the anvil head 320 to enable the extension portion 364 of the buttress member 360 to release from being sandwiched between a proximal end portion of the anvil cap 310 and a distal end portion of the anvil head 320, enabling the entire anvil buttress member 360 to separate from the anvil assembly 300.

As appreciated, any of the presently disclosed buttress members may have any suitable geometric configuration and may be supported on the anvil assembly and/or the cartridge assembly. Further, any of the buttress members of the present disclosure may be fabricated from surgical grade, biocompatible, non-absorbable material (i.e. permanent) or absorbable material (i.e. non-permanent) mesh or material desirably impregnated with an adhesive, sealant and/or other medicament. It is also contemplated that each portion may be a composite of both a non-absorbable and an absorbable material. Suitable materials for the fabrication of the buttress members and suitable adhesives, sealants, and/or medicaments for impregnation in or application to the buttress members may be found, for example, in U.S. Pat. No. 7,942,890, the entire contents of which are incorporated by reference herein.

Figure 10:
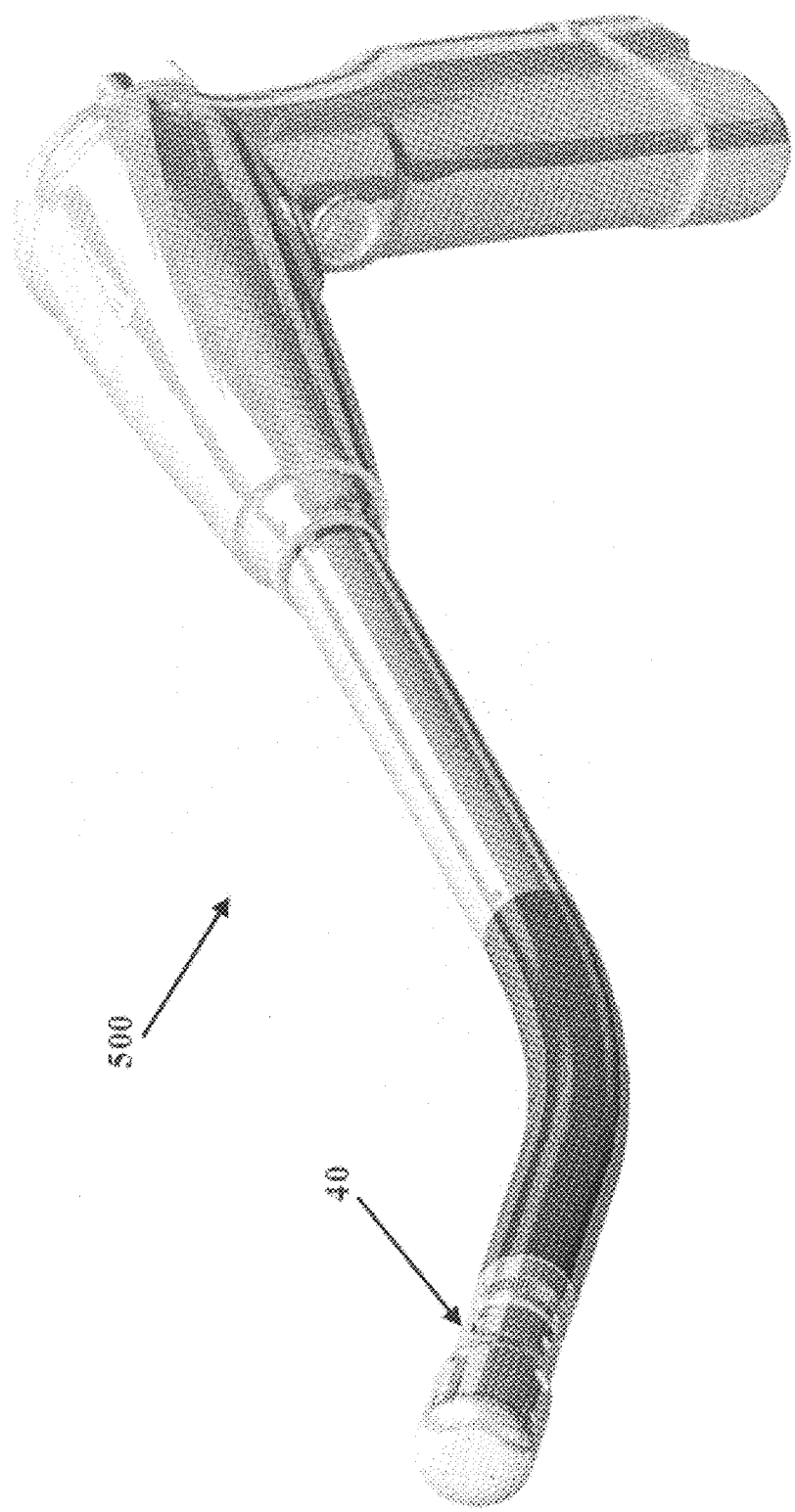
FIG. 10 is a schematic, perspective view of an exemplary electro-mechanical, powered handle configured to operate the end effector of the present disclosure.

As seen in FIG. 10, an electro-mechanical, powered surgical handle 500 is shown for use with end effector 40 of the present disclosure. Electro-mechanical, powered surgical handle 500 may include a source of power (e.g., a battery, etc.), a motor, and a circuit board (not shown) or the like.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Indeed, any combination of any of the presently disclosed elements and features is within the scope of the present disclosure. Accordingly, the subject matter of the present disclosure is not to be limited by what has been particularly shown and described.

The invention claimed is:

1. A circular stapler comprising:
a handle assembly;
an elongate body that extends from the handle assembly;
a cartridge assembly mounted on a distal end portion of the elongate body and being movable relative to the distal end portion of the elongate body between a first position and a second position, the cartridge assembly being positioned adjacent to the distal end portion of the elongate body in the first position and spaced from the distal end portion of the elongate body in the second position, the cartridge assembly including a tissue engaging surface that extends to an annular edge;
a cartridge buttress member having a body portion and an extension portion that extends from the body portion of the cartridge buttress member so that when the cartridge assembly is disposed in the first position, the body portion is supported on the tissue engaging surface of the cartridge assembly and the extension portion extends over the annular edge of the tissue engaging surface so that the extension portion is secured between the elongate body and the cartridge assembly to maintain the buttress member supported on the cartridge assembly; and
a spring assembly secured between the cartridge assembly and the distal end portion of the elongate body, the spring assembly adapted to pull the cartridge assembly toward the distal end portion of the elongate body to maintain the cartridge assembly in close approximation with the distal end portion of the elongate body when the cartridge assembly is disposed in the first position, the spring assembly including at least one spring that provides a spring force sufficient to trap the extension portion of the cartridge buttress member between the elongate body and the cartridge assembly when the cartridge assembly is disposed in the first position, the at least one spring being movable with the cartridge assembly to release the extension portion of the cartridge buttress member from between the elongate body and the cartridge assembly when the cartridge assembly is moved toward the second position.

2. The circular stapler of claim 1, wherein the cartridge assembly includes at least one pusher that drives the cartridge assembly toward the second position upon the firing of the circular stapler and against the spring force of the at least one spring, wherein the cartridge assembly moves to the second position and releases the extension portion of the cartridge buttress member from between the elongate body and the cartridge assembly, and wherein the body portion of the cartridge buttress member separates from the tissue engaging surface of the cartridge assembly upon the formation of fasteners supported in fastener retaining slots defined in the tissue engaging surface of the cartridge assembly.

3. The circular stapler of claim 1, further comprising an anvil assembly that is selectively movable relative to the cartridge assembly between an approximated position and an unapproximated position.

4. The circular stapler of claim 3, further comprising an anvil buttress member supported on a tissue engaging surface of the anvil assembly.

5. The circular stapler of claim 4, wherein the anvil buttress member has a body portion and an extension portion that extends from the body portion thereof, the anvil assembly including a clamping assembly that secures the extension portion of the anvil buttress member to the anvil assembly so that the body portion of the anvil buttress member is supported over a tissue engaging surface of the anvil assembly.

6. The circular stapler of claim 5, wherein the clamping assembly includes a clamp that is spring loaded to maintain the extension portion of the anvil buttress member secured to the anvil assembly.

7. The circular stapler of claim 6, further comprising a knife assembly including a knife, the clamp including a lockout assembly that retains the clamp in a locked arrangement to maintain the extension portion of the anvil buttress member secured to the anvil assembly, the knife being movable to position the lockout assembly in an unlocked arrangement so that the spring force from the spring loaded clamp moves the clamp to release the extension portion of the anvil buttress member.

8. A circular stapler comprising:
a handle assembly;
an elongate body that extends from the handle assembly;
an end effector mounted on a distal end portion of the elongate body, the end effector including an anvil assembly and a cartridge assembly, the anvil assembly being selectively movable relative to the cartridge assembly between an approximated position and an unapproximated position; and
an anvil buttress member supported on the anvil assembly, the buttress member having a body portion and an extension portion that extends from the body portion, the anvil assembly including a spring loaded clamp that secures the extension portion of the anvil buttress member to the anvil assembly so that the body portion of the anvil buttress member is supported over a tissue engaging surface of the anvil assembly, the spring loaded clamp including a lockout assembly that retains the spring loaded clamp in a locked arrangement to maintain the extension portion of the anvil buttress member secured to the anvil assembly.

9. A circular stapler comprising:
a handle assembly;
an elongate body that extends from the handle assembly;
an end effector mounted on a distal end portion of the elongate body, the end effector including an anvil assembly and a cartridge assembly, the anvil assembly being selectively movable relative to the cartridge assembly between an approximated position and an unapproximated position;
an anvil buttress member supported on the anvil assembly, the buttress member having a body portion and an extension portion that extends from the body portion, the anvil assembly including a spring loaded clamp that secures the extension portion of the anvil buttress member to the anvil assembly so that the body portion of the anvil buttress member is supported over a tissue engaging surface of the anvil assembly; and
a knife assembly including a knife, the spring loaded clamp including a lockout assembly that retains the spring loaded clamp in a locked arrangement to maintain the extension portion of the anvil buttress member secured to the anvil assembly, the knife being movable to position the lockout assembly in an unlocked arrangement, the spring loaded clamp being configured to release the extension portion of the anvil buttress member when the lockout assembly is disposed in the unlocked arrangement.

10. The circular stapler of claim 8, wherein the cartridge assembly is movable relative to the distal end portion of the elongate body between a first position and a second position, the cartridge assembly being positioned adjacent to the distal end portion of the elongate body in the first position and spaced from the distal end portion of the elongate body in the second position.

11. The circular stapler of claim 10, wherein the cartridge assembly supports a cartridge buttress member that is secured between the elongate body and the cartridge assembly when the cartridge assembly is disposed in the first position, wherein a movement of the cartridge assembly to the second position releases the cartridge buttress member from between the elongate body and the cartridge assembly.

12. The circular stapler of claim 8, wherein the lockout assembly includes a clamp engaging finger and the spring loaded clamp defines a recess configured to retain the clamp engaging finger to selectively lock the spring loaded clamp in a locked arrangement.

13. The circular stapler of claim 12, wherein the recess of the spring loaded clamp is configured to frictionally engage the clamp engaging finger to retain the clamp engaging finger therein.

14. The circular stapler of claim 13, wherein axial movement of the clamp engaging finger disengages the clamp engaging finger from the recess of the spring loaded clamp and positions the spring loaded clamp in an unlocked arrangement such that the extension portion of the anvil buttress member is released from the anvil assembly.

* * * * *